(12) United States Patent
Lichtblau

(10) Patent No.: US 9,289,527 B1
(45) Date of Patent: Mar. 22, 2016

(54) UV DISINFECTION SYSTEM WITH BALLAST CURRENT MONITORING

(71) Applicant: George J. Lichtblau, New Canaan, CT (US)

(72) Inventor: George J. Lichtblau, New Canaan, CT (US)

( * ) Notice: Subject to any disclaimer, the term of this patent is extended or adjusted under 35 U.S.C. 154(b) by 0 days.

(21) Appl. No.: 14/714,905

(22) Filed: May 18, 2015

(51) Int. Cl.
*A61L 2/10* (2006.01)
*A61L 2/24* (2006.01)

(52) U.S. Cl.
CPC .... *A61L 2/24* (2013.01); *A61L 2/10* (2013.01)

(58) Field of Classification Search
CPC ......... A61L 2/10; A61L 2/24; A61L 2202/14; A61L 2202/122; A61L 9/20; A61L 2/0047; A61L 2/26; A61L 2/28; A23L 3/28
See application file for complete search history.

(56) References Cited

U.S. PATENT DOCUMENTS

| | | | | |
|---|---|---|---|---|
| 6,171,548 B1 * | 1/2001 | Rose | .......................... | A61L 2/02 422/128 |
| D511,621 S * | 11/2005 | Lindamood | .................. | D14/299 |
| 8,378,323 B1 * | 2/2013 | Spann | ....................... | A61L 2/10 250/455.11 |
| 8,623,275 B2 | 1/2014 | Deshays | | |
| 8,636,950 B2 | 1/2014 | Deshays | | |
| 2003/0034459 A1 * | 2/2003 | Bonin | ........................ | A61L 2/06 250/491.1 |
| 2006/0278075 A1 | 12/2006 | Blackner | | |
| 2010/0266445 A1 * | 10/2010 | Campagna | ................ | A61L 2/10 422/23 |
| 2013/0020942 A1 * | 1/2013 | Voronov | ................. | H01J 61/28 315/116 |
| 2014/0287154 A1 * | 9/2014 | Kaiser | ...................... | A62D 5/00 427/520 |
| 2015/0062893 A1 * | 3/2015 | Lynn | ......................... | A61L 2/10 362/231 |

* cited by examiner

*Primary Examiner* — Brooke Purinton
(74) *Attorney, Agent, or Firm* — Preti Flaherty Beliveau & Pachios LLP

(57) ABSTRACT

An ultraviolet radiation system to decontaminate small objects such as TV remote controls, hospital bed controls, cell phones, computer tablets and the like which are present in a hospital or other health care facility. The system includes a plurality of UVC lamps arranged in a table top sized housing and having a UVC transmissive shelf in the housing for support of objects to be decontaminated. The system has a microprocessor based controller and can kill *Clostridium difficile* and other pathogens to thereby decontaminate items in 30 seconds or less.

29 Claims, 4 Drawing Sheets

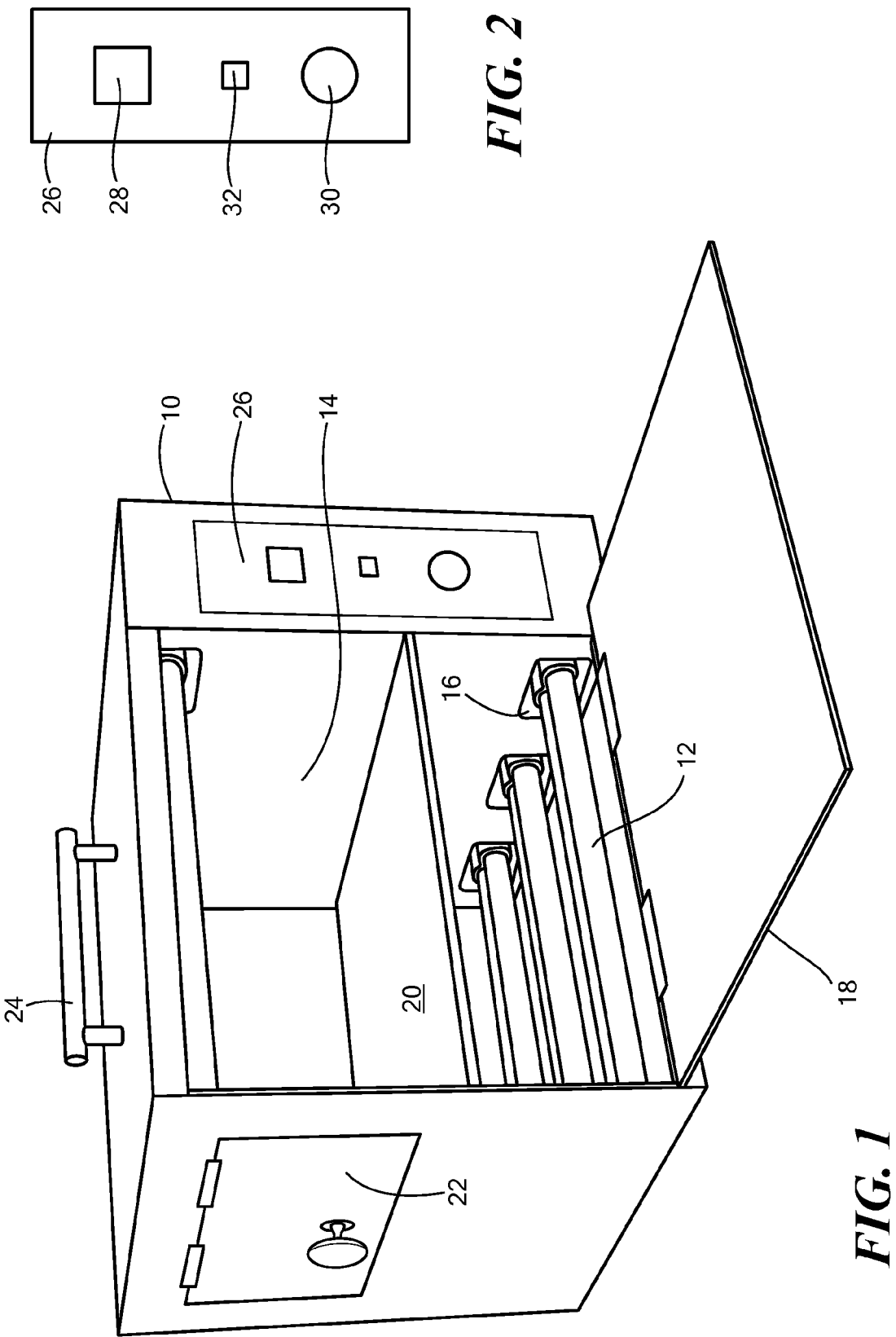

UV DISINFECTION SYSTEM WITH BALLAST CURRENT MONITORING

STATEMENT REGARDING FEDERALLY SPONSORED RESEARCH OR DEVELOPMENT

N/A

BACKGROUND OF THE INVENTION

Hospital acquired infections can infect patients, healthcare providers and visitors in a hospital environment, and infections can be passed from one person to another by contact with contaminated fixtures, surfaces or other objects in a hospital or other healthcare facility. One product for addressing the matter of decontamination, particularly in a hospital setting, is described in U.S. Pat. No. 8,791,441 of the same inventor as the present invention. This patent shows a system for decontamination by UVC radiation of surfaces of a hospital room or other facility and of the air in the room.

There is a need for a convenient and cost effective manner to decontaminate small items typically found in a hospital environment such as hospital bed controls, TV remote controls, cellphones, computer tablets, and the like.

BRIEF SUMMARY OF THE INVENTION

The present invention provides a UVC disinfection system housed in a tabletop enclosure similar in size to a toaster oven or microwave oven. A door permits access to a chamber in which small items to be decontaminated can be disposed. The system produces UVC radiation of sufficient dosage to kill pathogens including *Clostridium difficile* on the items in the chamber in a rapid, simple and reliable manner. The system in one embodiment comprises a housing containing a plurality of UVC lamps disposed at the top and bottom of the housing, a UVC transmissive shelf in the chamber for supporting items to be decontaminated and an electronic controller for control of the ballasts for the UVC lamps and for control of system operation.

The germicidal lamps are typically low pressure, high output mercury or amalgam lamps that have an extremely high conversion efficiency of 35% of input power to radiation at 253.7 nm (usually referred to as 254 nm). The UVC lamps are made of pure quartz designed to pass radiation at 253.7 nm but not cause ozone generation. The quartz is quite brittle and if accidently broken causes scatter of quartz particles over a wide area. To eliminate this potential problem, each lamp tube is encased in an FEP (Teflon) sleeve to contain any fragments of quartz if broken. FEP is one of the few plastics that have a very low attenuation of UVC radiation and is also unaffected by the temperature of the quartz envelope when the lamp is energized. The UVC lamps are driven by one or more electronic ballasts which can operate from a wide variety of AC power sources. In a preferred embodiment, the housing is made of aluminum with a hinged and locking front cover. A shelf of pure quartz is provided in the chamber and on which items to be decontaminated can be placed.

The system is controlled by an electronic controller which typically is a microprocessor based controller. The door has a locking mechanism to maintain the door in closed position and is associated with a safety switch to prevent operation of the system when the door is open. An alpha, numeric or alpha numeric display is provided on the housing to indicate time remaining for completion of a decontamination cycle and to indicate system status. Audible and/or visual indicators can also be provided to signify system conditions including error conditions if the lamps or the system are not operating properly. A single pushbutton switch is provided on a control panel to start a decontamination cycle. The pushbutton can be of the lighted type which illuminates to indicate that power is applied to the system.

The housing can include a side door or slot to enable wires or cords of devices being decontaminated to be threaded from outside the housing into the chamber. The wired or corded devices can be for example, a hospital telephone or hospital bed control. The side door may also have a safety switch to prevent operation of the system if the door is opened beyond a small amount necessary to accommodate the device cord.

BRIEF DESCRIPTION OF THE SEVERAL VIEWS OF THE DRAWINGS

The invention will be more fully understood from the following detailed description in conjunction with the drawings in which:

FIG. 1 is a pictorial view of one embodiment of a system in accordance with invention;

FIG. 2 is a diagrammatic view of a control panel of the embodiment of FIG. 1;

DETAILED DESCRIPTION OF THE INVENTION

Figure 3:
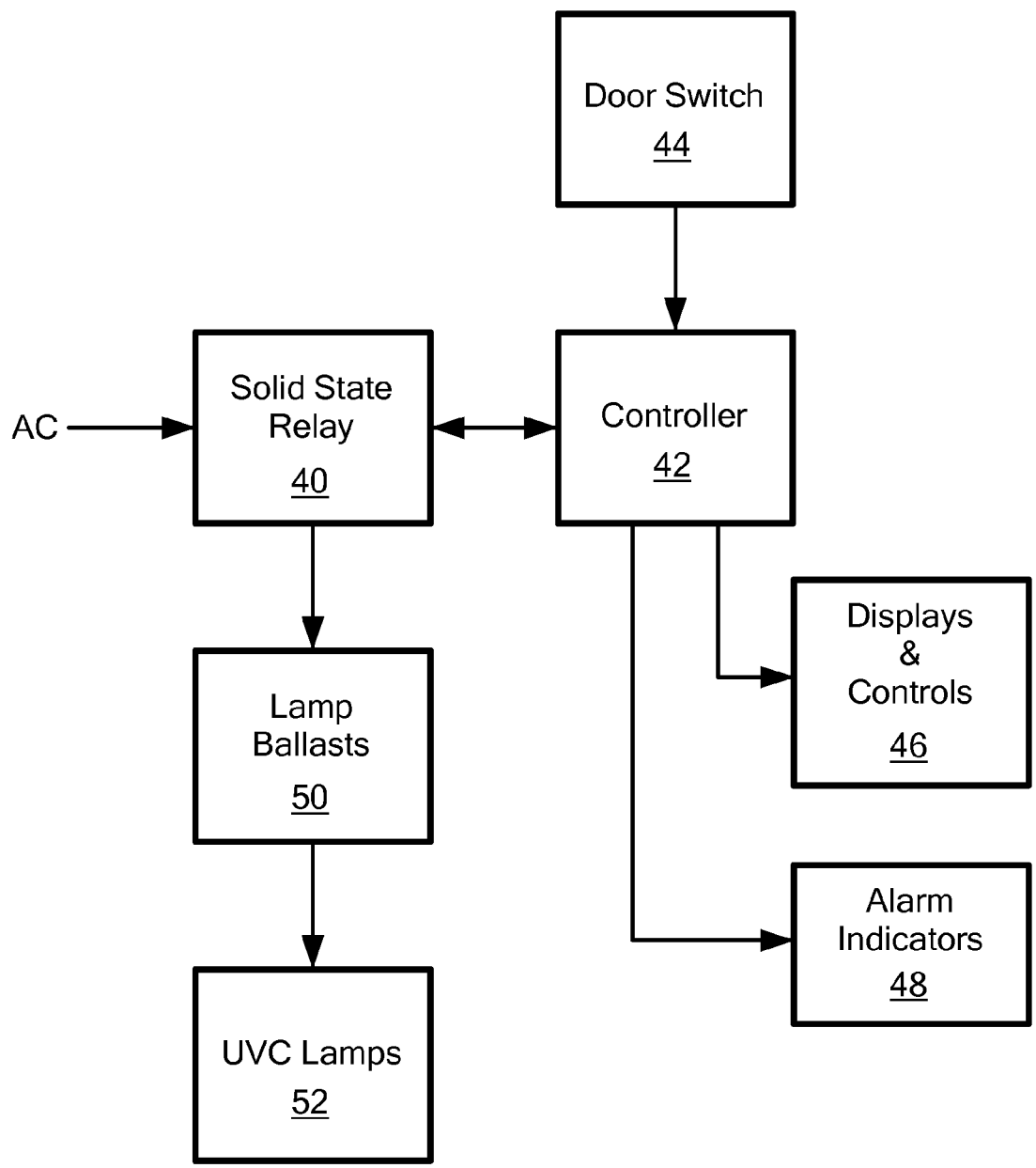
FIG. 3 is a block diagram of a system in accordance with the invention.

One embodiment of a UVC disinfection system in accordance with the invention is shown in FIG. 1. A housing or enclosure 10 contains a plurality of UVC lamps 12 at the top and bottom of a chamber 14. In the illustrated embodiment three lamps are arranged at the bottom of the chamber and three lamps are arranged at the top of the chamber. The lamps are in the form of U shaped tubes having an electrical connector at one end thereof and which are pluggable at one end into associated sockets 16 positioned in the housing 10. The lamps are typically high output, low pressure mercury or amalgam UVC generating lamps such as Light Sources model LTC 24W/2G11/FEP Coated. The length of the lamps is typically about 12 inches. In the illustrated embodiment sufficient UVC radiation is provided to kill 99% of pathogens in 30 seconds or less. Another lamp type is 20 inches long and has a 55 watt capacity The housing 10 can be made of any suitable material and in the illustrated embodiment is aluminum which can be oxidized on the interior walls of the chamber to enhance the reflectance of UVC radiation from the lamps and heighten system efficiency.

Preferably each lamp is covered by a protective sleeve to avoid shattering of the lamp quartz glass in the event of breakage. FEP (Teflon) is preferred because it is UV transmissive with little attenuation and can easily withstand the operating temperature of the lamps. A door 18 is hinged to the housing 10 and when open permits access to the chamber 14 for placement and removal of items to be decontaminated. A quartz shelf 20 is provided in the chamber approximately midway of the chamber height. The quartz shelf is UV transmissive and provides support for items to be decontaminated. Such items are typically those found in a hospital or healthcare environment and include hospital bed controls, TV remote controls, cellphones, computer tablets, computer keyboards and the like. A side door 22 is provided on a side of enclosure 10 to provide access for device cords which may be attached to items to be decontaminated, such as for example hospital bed controls. The housing may include a handle 24 for carrying the system.

The UVC lamps are driven by a power source having electronic ballasts which start the lamps and regulate the current in each lamp to assure proper and safe operation. Each lamp may be driven by one electronic ballast or a single ballast may drive multiple lamps depending upon the particular lamps and ballasts employed. The electronic ballasts may operate from a standard 110 volt 60 Hz power source or from a 220 volt 50 Hz source or from a dual voltage or other suitable source. A removable power cord may be employed for convenience of system transport.

The system is controlled by a microprocessor based microcontroller typically contained on a control board disposed within the housing. The ballasts and power components in the illustrated embodiment are disposed on one side of the housing behind a control panel 26 which in the illustrated embodiment is on the right side of the front of the housing. The control panel 26 is illustrated diagrammatically in FIG. 2 and includes a display 28 such as a two digit digital display to indicate countdown of remaining time during a decontamination cycle and to indicate system messages such as error conditions. An audio annunciator 30 such as a Sonalert is provided to audibly indicate, such as by a beep, that an operating cycle has ended. The annunciator can also provide distinguishable sounds to denote one or more error conditions. A control switch 32 is provided to activate the system. The control switch can be of the illuminated type which illuminates when actuated to start a decontamination cycle.

A block diagram of the system is illustrated in FIG. 3. AC input power is provided to a solid state relay 40 and thence to a controller 42 which governs system operation. The solid state relay is coupled to the lamp ballasts 50 which drive the UVC lamps 52. Over current protection devices such a fuse or circuit breaker may be provided. The controller 42 is coupled to door switch 44, to displays and controls 46 and to alarm indicators 48. The display and controls 46 include the displays or indicators of system conditions and controls for system operation, such as those shown in the control panel of FIG. 2. The door switches 44 include a switch for door 18 and door 22. Each of the switches will cause the controller to prevent system operation or shut down operation if a door is opened during an operating cycle. The door can include a locking mechanism which prevents opening of the door during system operation. The side door 22 can include a mechanism to limit the amount of door opening such that a minimal opening is provided that is sufficient to allow passage of an electrical cord to minimize leakage of UV radiation from the chamber 14 into the room in which the system is operating. The side door may have a slot or indented area to accommodate the cord of an item placed in the chamber.

The system typically operates for a predetermined period of time as governed by a time period set in the controller. Upon activation of the system by pushing the control switch 32, the lamps are turned on for the specified period of time and are turned off when the time period ends. The countdown of the operating time is shown in display 28 on the front panel.

The controller monitors the current to each of the electronic ballasts to insure that all of the lamps are operating properly. If the current is less than the designated reference value, the controller will turn off the UVC lamps and display a message on front panel display 28. Typically, the current monitor signal is converted to a digital signal by means of an analog to digital converter for comparison with a stored reference value. In order to determine which UVC lamp is not working properly, the system includes a diagnostic cycle by which the lamps can be turned on when the enclosure door is open. In this manner an operator can see which lamp is not working and have it replaced. A diagnostic cycle can be initiated for example by pressing the start button 32 multiple times within a designated period of time. For example, pressing the start button five times within 5 seconds will cause all of the lamps to be turned on for visual inspection.

Figure 4:
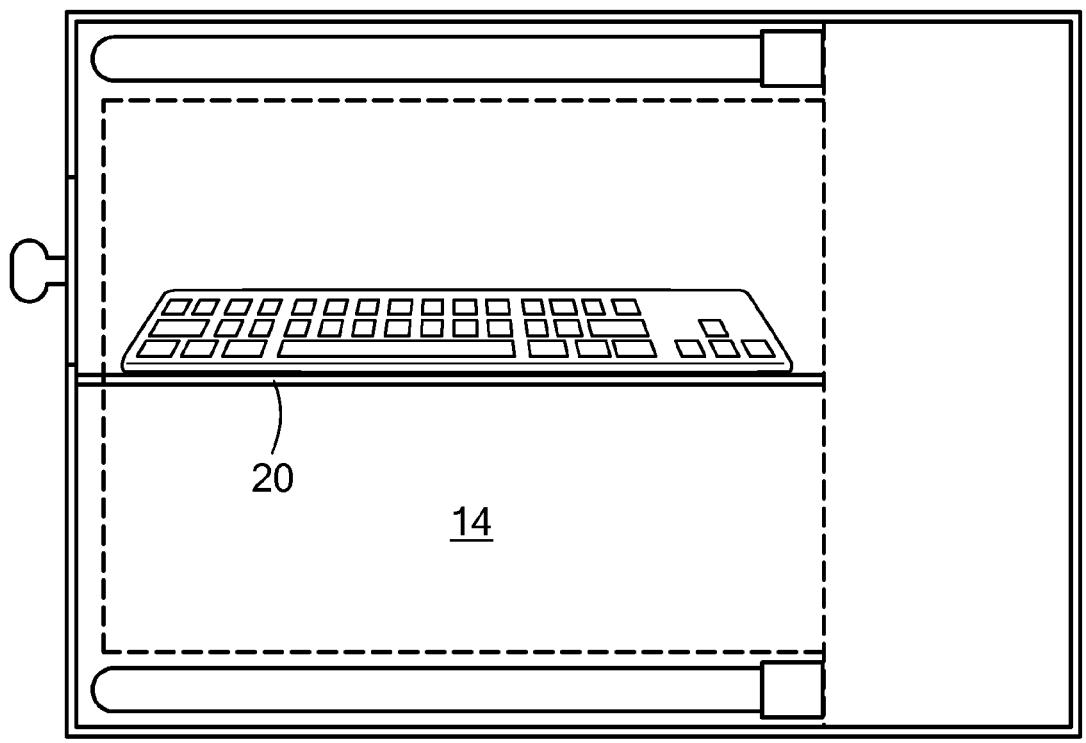
FIG. 4 is an elevation view of the system illustrating an item in place for contamination.
Figure 5:
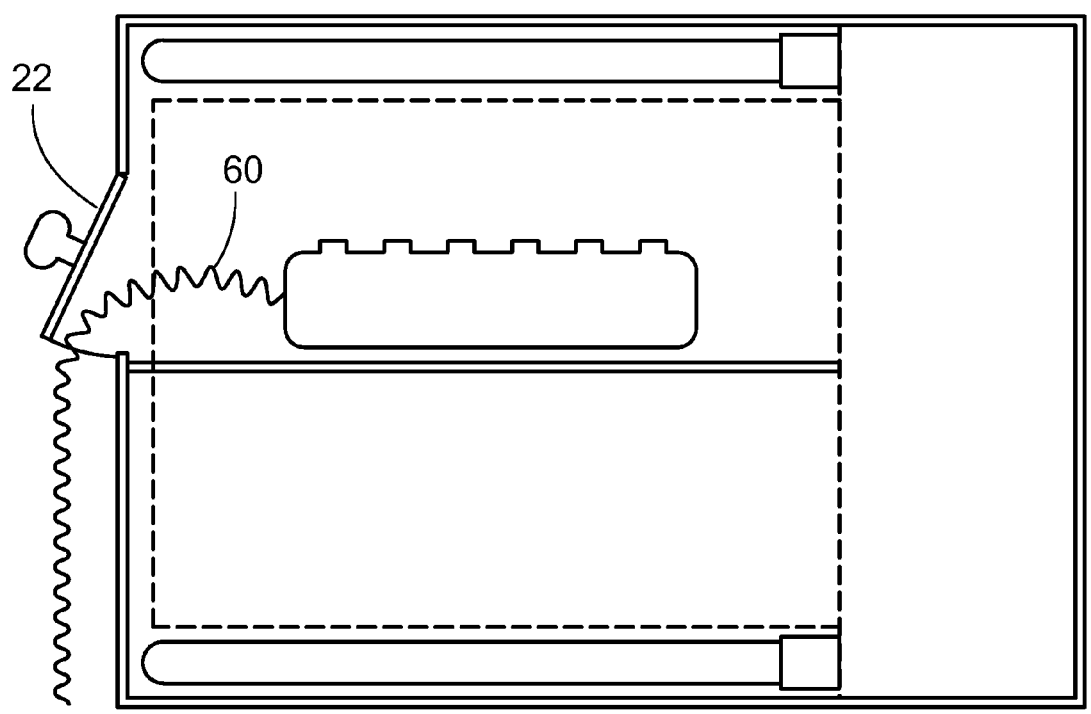
FIG. 5 is an elevation view of the system with a corded item in place for decontamination.

FIG. 4 illustrates a computer keyboard supported on the quartz shelf disposed in the chamber 14 for decontamination. A device having an electrical cord as illustrated in FIG. 5 is disposed on the shelf 20 and with the cord 60 threaded through a bottom opening in the side door 22 shown in its tilted open position.

It will be appreciated that the invention is not to be limited by the particular embodiment shown and that modifications and alternative implementations are contemplated and are within the intended scope of the invention. For example, the number and type of UVC lamps can vary and the physical configuration of the system may take different forms. Accordingly, the invention is not to be limited by what has been particularly shown and described except as defined by the appended claims.

What is claimed is:

1. A table top sized ultraviolet system for disinfecting small items comprising:
    a housing having a chamber therein and having a top, a bottom, side walls and an openable door;
    a plurality of UVC lamps disposed at the bottom of the chamber and a plurality of UVC lamps disposed at the top of the chamber and arranged to substantially flood the chamber with UVC radiation;
    a UVC transmissive shelf disposed in the chamber for supporting items to be decontaminated;
    a power source having one or more ballasts to drive the UVC lamps;
    an electronic controller to control operation of the system including the timing of a decontamination cycle and the monitoring of current to the ballasts;
    the electronic controller operative to provide a diagnostic cycle during which the UVC lamps are turned on with the door open to permit visual inspection of the lamps;
    a door switch associated with the door and operative to provide a signal to the controller to prevent or discontinue system operation when the door is open during a decontamination cycle; and
    a side door with a slot to permit devices that are connected to a wire to be placed on the shelf in the housing for decontamination, and with the device wire extending through the slot.

2. The system of claim 1 wherein the chamber has side walls which are reflective to UVC radiation.

3. The system of claim 2 wherein the housing is made of aluminum.

4. The system of claim 3 wherein the side walls of the chamber are oxidized to enhance UVC reflection.

5. The system of claim 1 wherein the controller measures the total current drawn by the lamps and compares the total current to a known value stored in the controller.

6. The system of claim 5 wherein a current monitor signal is converted to a digital level by means of an analog-to-digital converter.

7. The system of claim 1 wherein the controller includes a microprocessor with a built in analog-to-digital converter.

8. The system in claim 1 wherein the lamps are high output mercury or amalgam UVC lamps.

9. The system in claim 1 wherein the lamps are either approximately twelve (12) inches long and operate at 24 watts or twenty (20) inches long and operate at 55 watts.

10. The system in claim 1 wherein the ballasts can operate from 120 VAC 60 Hertz, 220 VAC 50 Hertz or 100-277 VAC 50/60 Hertz depending upon the selection of the ballast.

11. The system of claim 10 wherein the ballast receive AC power via a removable power cord.

12. The system of claim 1 wherein the power source is protected from over current by means of a resettable thermal circuit breaker or a fuse.

13. The system of claim 1 where the housing has a control panel on one side thereof.

14. The system of claim 13 wherein the control panel has a visual alpha or alpha/numeric display.

15. The system of claim 14 wherein the display is a two digit display indicating the time remaining in the decontamination cycle.

16. The system of claim 14 wherein the display counts down in seconds indicating the remaining time in the decontamination cycle.

17. The system of claim 14 wherein the control panel has an audio annunciator.

18. The system of claim 17 wherein the annunciator is a Sonalert.

19. The system of claim 17 wherein the annunciator will emit one audio signal to indicate the end of a decontamination cycle and a different signal to indicate an error condition.

20. The system of claim 13 wherein the control panel contains a push button switch to start a decontamination cycle.

21. The system of claim 20 wherein the switch is lighted to indicate power is applied to the system.

22. The system of claim 1 wherein there is sufficient UVC intensity to kill at least 99% of *Clostridium difficile* in less than 30 seconds.

23. The system of claim 1 wherein there is sufficient UVC intensity to kill at least 99.9% of *Clostridium difficile* in 30 seconds.

24. The system of claim 1 wherein the housing has a side door to accommodate the electrical cord of objects placed on the shelf in the chamber.

25. The system of claim 1 including a safety switch associated with the side door to inhibit the operation of the system if the side door is open.

26. The system of claim 25 where the safety switch will turn off the UVC lamps if they are operating when the side door is opened and will initiate a sequence of audio and visual messages to indicate that system operation was aborted prior to completion.

27. The system of claim 1 wherein the shelf is a quartz shelf which is UVC transmissive.

28. The system of claim 1 wherein the plurality of UVC lamps include three lamps mounted at the top of the chamber and three lamps mounted at in the bottom of the chamber.

29. The system of claim 1 wherein the UVC lamps are each U-shaped with an electrical convertor at one end thereof pluggable into a socket in the chamber.

* * * * *